US007918902B2

(12) United States Patent
Hercouet et al.

(10) Patent No.: US 7,918,902 B2
(45) Date of Patent: Apr. 5, 2011

(54) PROCESS FOR LIGHTENING OR PROCESS FOR DIRECT DYEING OR OXIDATION DYEING OF KERATIN FIBERS IN THE PRESENCE OF AT LEAST ONE AMMONIUM SALT AND DEVICE THEREFOR

(75) Inventors: Leïla Hercouet, Neuilly Plaisance (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/642,513

(22) Filed: Dec. 18, 2009

(65) Prior Publication Data

US 2010/0178264 A1    Jul. 15, 2010

Related U.S. Application Data

(60) Provisional application No. 61/151,255, filed on Feb. 10, 2009, provisional application No. 61/151,619, filed on Feb. 11, 2009.

(30) Foreign Application Priority Data

Dec. 19, 2008  (FR) ..................... 08 07287
Dec. 19, 2008  (FR) ..................... 08 07290

(51) Int. Cl.
    *A61Q 5/10*    (2006.01)
(52) U.S. Cl. ............. 8/405; 8/406; 8/407; 8/426; 8/462; 8/463; 8/602; 8/604; 8/111; 132/202; 132/208
(58) Field of Classification Search ............. 8/405, 406, 8/407, 426, 431, 462, 463, 602, 604, 111; 132/202, 208
See application file for complete search history.

(56) References Cited

U.S. PATENT DOCUMENTS

| | | | |
|---|---|---|---|
| 3,100,739 A | 8/1963 | Kaiser et al. | |
| 3,369,970 A | 2/1968 | McLaughlin et al. | |
| 3,629,330 A | 12/1971 | Brody et al. | |
| 3,861,868 A | 1/1975 | Milbrada | |
| 4,138,478 A | 2/1979 | Reese et al. | |
| 4,170,637 A | 10/1979 | Pum | |
| 4,226,851 A | 10/1980 | Sompayrac | |
| 4,357,141 A | 11/1982 | Grollier et al. | |
| 4,366,099 A | 12/1982 | Gaetani et al. | |
| 4,488,564 A | 12/1984 | Grollier et al. | |
| 4,725,282 A | 2/1988 | Hoch et al. | |
| 4,845,293 A | 7/1989 | Junino et al. | |
| 5,021,066 A | 6/1991 | Aeby et al. | |
| 5,259,849 A | 11/1993 | Grollier et al. | |
| 5,364,414 A | 11/1994 | Lang et al. | |
| 5,817,155 A | 10/1998 | Yasuda et al. | |
| 6,010,541 A | 1/2000 | De La Mettrie et al. | |
| 6,074,439 A | 6/2000 | De La Mettrie et al. | |
| 6,129,770 A | 10/2000 | Deutz et al. | |
| 6,156,713 A | 12/2000 | Chopra et al. | |
| 6,165,444 A | 12/2000 | Dubief et al. | |
| 6,190,421 B1 | 2/2001 | Rondeau et al. | |
| 6,206,935 B1 | 3/2001 | Onitsuka et al. | |
| 6,238,653 B1 | 5/2001 | Narasimhan et al. | |
| 6,251,378 B1 | 6/2001 | Laurent et al. | |
| 6,260,556 B1 | 7/2001 | Legrand et al. | |
| 6,277,154 B1 | 8/2001 | Lorenz | |
| 6,277,155 B1 | 8/2001 | De La Mettrie et al. | |
| 6,365,136 B1 | 4/2002 | Lauscher et al. | |
| 6,423,100 B1 | 7/2002 | Lang et al. | |
| 6,447,552 B1 | 9/2002 | Golinski | |
| 6,645,258 B2 | 11/2003 | Vidal et al. | |
| 6,660,045 B1 | 12/2003 | Hoeffkes et al. | |
| 6,695,887 B2 | 2/2004 | Cottard et al. | |
| 6,800,098 B1 | 10/2004 | Allard et al. | |
| 7,135,046 B2 | 11/2006 | Audousset | |
| 7,153,331 B2 | 12/2006 | Desenne et al. | |
| 7,217,298 B2 | 5/2007 | Legrand et al. | |
| 7,285,137 B2 | 10/2007 | Vidal et al. | |
| 7,442,215 B2 | 10/2008 | Audousset et al. | |
| 7,458,993 B2 | 12/2008 | Cottard et al. | |
| 7,494,513 B2 | 2/2009 | Kravtchenko et al. | |
| 7,575,605 B2 | 8/2009 | Legrand | |
| 7,651,533 B2 | 1/2010 | Legrand | |
| 7,651,536 B2 | 1/2010 | Cottard et al. | |
| 7,766,977 B2 | 8/2010 | Cottard | |

(Continued)

FOREIGN PATENT DOCUMENTS

CA      1 268 421      5/1990

(Continued)

OTHER PUBLICATIONS

French Search Report for FR 0807287, dated Oct. 13, 2009.
French Search Report for FR 0807290, dated Oct. 14, 2009.
English language abstract of DE 38 14 356 A1, Sep. 8, 1988.
English language abstract of DE 10 2005 059 647 A1, Jun. 14, 2007.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.

(Continued)

*Primary Examiner* — Eisa B Elhilo
(74) *Attorney, Agent, or Firm* — Finnegan, Henderson, Farabow, Garrett & Dunner LLP

(57) ABSTRACT

The present disclosure relates to a process for lightening or dyeing keratin fibers, for example, human keratin fibers such as the hair, comprising applying to the keratin fibers: (a) an anhydrous cosmetic composition (A) comprising at least one fatty substance and at least one surfactant; (b) a cosmetic composition (B) comprising at least one ammonium salt; and (c) a composition (C) comprising at least one oxidizing agent; when the process is a process for dyeing keratin fibers, said cosmetic composition (B) further comprises at least one oxidation dye and/or at least one direct dye. The present disclosure also relates to a multi-compartment device comprising the disclosed compositions for lightening or dyeing keratin fibers.

16 Claims, No Drawings

U.S. PATENT DOCUMENTS

| | | |
|---|---|---|
| 2003/0190297 A1 | 10/2003 | Narasimhan et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | LeGrand |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1* | 7/2009 | Hercouet et al. ........... 424/70.31 |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 A1 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 A1 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 A1 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 A1 | 11/2005 |
| EP | 1 449 512 | 8/2006 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 A2 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 A1 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 A1 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 A1 | 3/2006 |
| WO | WO 2007/006418 | 1/2007 |
| WO | WO 2007/096027 | 8/2007 |

| | | |
|---|---|---|
| WO | WO 2008/021641 | 2/2008 |
| WO | WO 2008/096497 | 8/2008 |
| WO | WO 2008/138844 | 11/2008 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 20 05 076, dated Aug. 6, 1970.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 716 840, dated Nov. 2, 2006.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 892 623, dated May 4, 2007.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/096027, dated Aug. 30, 2007.
English language Abstract of WO 2008/096497, dated Aug. 14, 2008.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07288, dated Nov. 4, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.

Notice of Allowance mailed Aug. 26, 2010, in U.S. Appl. No. 12/642,637.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

PROCESS FOR LIGHTENING OR PROCESS FOR DIRECT DYEING OR OXIDATION DYEING OF KERATIN FIBERS IN THE PRESENCE OF AT LEAST ONE AMMONIUM SALT AND DEVICE THEREFOR

This application claims benefit of U.S. Provisional Application Nos. 61/151,255, filed Feb. 10, 2009, and 61/151,619, filed Feb. 11, 2009. This application also claims benefit of priority under 35 U.S.C. §119 to French Patent Application Nos. 0807287 and 0807290, filed Dec. 19, 2008.

The present disclosure relates to a process for lightening or a process for dyeing keratin fibers, for example, human keratin fibers such as hair, comprising applying to the keratin fibers: an anhydrous cosmetic composition (A) comprising at least one fatty substance and at least one surfactant; a cosmetic composition (B) comprising at least one ammonium salt; and a composition (C) comprising at least one oxidizing agent. In addition, when the process according to the present disclosure is a process for dyeing keratin fibers, the composition (B) further comprises at least one dye.

The present disclosure also relates to a multi-compartment device which comprises a first compartment comprising the abovementioned anhydrous cosmetic composition (A), a second compartment comprising the abovementioned cosmetic composition (B), and a third compartment comprising the abovementioned composition (C).

Many people have been seeking for a long time to modify the color of their hair such as to hide their grey hair. To do this, there are essentially two types of coloration that have been developed.

The first type of coloration is permanent dyeing or oxidation dyeing, which uses dye compositions containing oxidation dye precursors, generally known as oxidation bases. These oxidation bases are colorless or weakly colored compounds, which, when combined with oxidizing products, can give rise, via a process of oxidative condensation, to colored compounds.

It is also known that the shades obtained with these oxidation bases may often be varied by combining them with couplers or dye modifiers, these being chosen from aromatic meta-diamines, meta-aminophenols, meta-diphenols and certain heterocyclic compounds, such as indole compounds. The variety of molecules used as oxidation bases and couplers allows a wide range of colors to be obtained.

The second type of dyeing is referred to as semi-permanent dyeing or direct dyeing which consists of applying to the keratin fibers direct dyes, which are colored and coloring molecules that have affinity for the fibers, in leaving them on for a time to allow the molecules to penetrate, by diffusion, into the fiber, and then in rinsing them off.

In order to perform these dyeing operations, the direct dyes used may be chosen from nitrobenzene, anthraquinone, nitropyridine, azo, xanthene, acridine, azine and triarylmethane direct dyes.

This type of process does not require the use of an oxidizing agent to develop the coloration. However, it is not excluded to use one in order to obtain a lightening effect along with the coloration. Such a process is then referred to as a direct dyeing or semi-permanent dyeing under lightening conditions.

Processes of permanent or semi-permanent dyeing under lightening conditions thus consist in using, along with the dye composition, an aqueous composition comprising at least one oxidizing agent, under alkaline pH conditions. The role of this oxidizing agent is, at least in part, to degrade the melanin of the hair, which, depending on the nature of the oxidizing agent present, leads to more less pronounced lightening of the fibers. Thus, for relatively weak lightening, the oxidizing agent is generally hydrogen peroxide. When more substantial lightening is desired, peroxygenated salts, for instance persulfates, are usually used in the presence of hydrogen peroxide.

Processes for lightening human keratin fibers consist in employing an aqueous composition comprising at least one oxidizing agent, under alkaline pH conditions. The role of this oxidizing agent is to degrade the melanin of the hair, which, depending on the nature of the oxidizing agent present, leads to more or less pronounced lightening of the fibers. Thus, for relatively weak lightening, the oxidizing agent is generally hydrogen peroxide. When greater lightening is required, peroxygenated salts are usually used, for instance persulfates, in the presence of hydrogen peroxide.

One of the difficulties encountered when implementing the lightening or lightening dyeing processes of the prior art arises from the fact that these processes are performed under alkaline conditions and that the alkaline agent commonly used is aqueous ammonia. The use of aqueous ammonia is advantageous in processes of this type. The reason for this is that it allows the pH of the composition to be adjusted to an alkaline pH to enable activation of the oxidizing agent. However, this alkaline agent also causes swelling of the keratin fiber, with raising of the scales, which promotes the penetration of the oxidizing agent, and also of the dyes, such as the oxidation dyes, into the fiber, and thus increases the efficacy of the dyeing reaction.

However, this basifying agent is very volatile, which users find disagreeable due to the strong, rather unpleasant odor of ammonia that is given off during the process.

Furthermore, the amount of ammonia given off makes it necessary to apply this agent in a larger amount than the amount required to form the process, in order to compensate for this loss. This is not without consequences on the user, who not only remains inconvenienced by the odor, but may also be confronted with greater risks of intolerance, for instance irritation of the scalp in the form, for example, of stinging.

With respect to the option of simply replacing all or some of the aqueous ammonia with at least one other standard basifying agent, this does not lead to compositions that are as efficient as those based on aqueous ammonia, since these basifying agents do not afford sufficient lightening of pigmented fibers in the presence of the oxidizing agent.

One aspect of the present disclosure is to propose lightening or dyeing processes of human keratin fibers performed in the presence of an oxidizing agent, which do not have the drawbacks of the existing processes, such as the drawbacks due to the presence of large amounts of aqueous ammonia, but which remain at least as efficient. The efficiency of lightening processes is based on the quality and homogeneity of the lightening, and the efficiency of dyeing processes is based on the dyeing power obtained, and also the chromaticity and the homogeneity of the coloration along the fiber.

One aspect of the present disclosure is to provide a process for lightening or dyeing keratin fibers, for example, human keratin fibers such as the hair wherein the following compositions are applied to the keratin fibers:
  (a) a cosmetic anhydrous composition (A) comprising at least one fatty substance and at least one surfactant;
  (b) a cosmetic composition (B) comprising at least one ammonium salt,
  (c) a composition (C) comprising at least one oxidizing agent;

when the process according to the present disclosure is a process for dyeing keratin fibers, the composition (B) further comprises at least one oxidation dye and/or at least one direct dye.

Thus, the use of the lightening process according to the present disclosure makes it possible to obtain lightening performance qualities equivalent or even superior to those obtained with the existing compositions, such as with compositions based on ammonium hydroxide.

The dyeing process according to the present disclosure leads to strong, sparingly selective colorations, or colorations that are uniform along the fiber.

Moreover, the processes according to the present disclosure employ compositions that do not give off an aggressive odor when they are applied to the hair or when they are prepared.

The present disclosure also relates to a multi-compartment device comprising, in a first compartment, an anhydrous cosmetic composition (A) comprising at least one fatty substance and at least one surfactant; in a second compartment, a cosmetic composition (B) comprising at least one ammonium salt, and also optionally at least one oxidation dye and/or at least one direct dye; and in a third compartment, a composition (C) comprising at least one oxidizing agent.

Other characteristics and advantages of the present disclosure will emerge more clearly on reading the description and the examples that follow.

In some embodiments, the human keratin fibers treated by the process according to the present disclosure are the hair.

As indicated previously, the disclosed dyeing process may comprise applying a cosmetic anhydrous composition (A) to the keratin fibers.

For the purposes of the present disclosure, the term "cosmetic anhydrous composition" means a cosmetic composition with a water content that may be equal to 0% or less than 5% by weight, for example, less than 2% by weight such as less than 1% by weight, relative to the weight of said composition. It should be noted that the water present in the composition may be "bound water", for instance the water of crystallization of salts or traces of water absorbed by the starting materials used in the preparation of the compositions according to the present disclosure.

The lightening process according to the present disclosure is performed in the presence of compositions not comprising a direct dye or an oxidation dye precursor (bases and couplers) usually used for the dyeing of human keratin fibers, or else, if they are present, their total content does not exceed 0.005% by weight relative to the weight of each composition. At such a content, only the composition would optionally be dyed, i.e. no coloration of the keratin fibers would be observed.

In some embodiments, the lightening process is performed without oxidation base, or coupler, or direct dye.

As has been mentioned, the anhydrous cosmetic composition (A) comprises at least one fatty substances.

The term "fatty substance," as used herein, means an organic compound that is insoluble in water at ordinary temperature (25° C.) and at atmospheric pressure (760 mmHg), i.e. solubility of less than 5%, for example, the solubility may be 1%, and further as an example, the solubility may be 0.1%. They have in their structure at least one chain containing at least two siloxane groups or one hydrocarbon-based chain comprising at least 6 carbon atoms. In addition, the fatty substances may be soluble in organic solvents under the same temperature and pressure conditions, for instance, may be be soluble in chloroform, ethanol, benzene, liquid petroleum jelly, or decamethyl cyclopentasiloxane.

According to the present disclosure, the fatty substances are chosen from compounds that are liquid or pasty at room temperature and atmospheric pressure.

The fatty substances can be chosen from $C_6$-$C_{16}$ lower alkanes, non-silicone oils of mineral, plant, animal or synthetic origin, fatty alcohols, fatty acids, esters of a fatty acid, esters of a fatty alcohol, non-silicone waxes, and silicones.

In some embodiments, the fatty alcohols, fatty esters, and fatty acids may contain at least one linear or branched, saturated or unsaturated hydrocarbon-based groups containing 6 to 30 carbon atoms, which is optionally substituted, for instance, with at least one hydroxyl groups (such as 1 to 4). If they are unsaturated, these compounds may comprise one to three conjugated or nonconjugated carbon-carbon double bonds.

Lower $C_6$-$C_{16}$ alkanes may be linear or branched, or possibly cyclic. By way of example, non-limiting mention may be made of hexane, undecane, dodecane, tridecane, isoparaffins, for instance, isohexadecane and isodecane.

Oils of mineral, plant, animal or synthetic origin that may be used in the composition of the present disclosure, non-limiting examples that may be mentioned include:

hydrocarbon-based oils of animal origin, such as perhydrosqualene;

triglycerides of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812 and 818 by the company Dynamit Nobel, jojoba oil and shea butter oil;

linear or branched hydrocarbons having more than 16 carbon atoms, of mineral or synthetic origin, such as volatile or nonvolatile liquid paraffins, and derivatives thereof, petroleum jelly, liquid petroleum jelly, polydecenes, hydrogenated polyisobutenes such as PARLEAM®, for example, liquid paraffins, petroleum jelly, liquid petroleum jelly, polydecenes, hydrogenated polyisobutenes such as PARLEAM®;

fluoro oils such as perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols suitable for use in the present disclosure may be chosen from saturated or unsaturated, linear or branched, alcohols comprising from 8 to 30 carbon atoms, for instance cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol.

The fatty acids that may be used in the anhydrous cosmetic composition (A) may be saturated or unsaturated carboxylic acids and contain from 6 to 30 carbon atoms such as from 9 to 30 carbon atoms. As non-limiting examples, the fatty acids may be chosen from myristic acid, palmitic acid, stearic acid, behenic acid, oleic acid, linoleic acid, linolenic acid, and isostearic acid.

With respect to the esters of fatty acid and/or of fatty alcohols other than the triglycerides mentioned above, non-limiting mention may be made of the esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters may be greater than or equal to 10.

The monoesters may be chose from, in a non-limiting manner, dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates; 2-ethylhexyl palmitate; 2-octyldecyl palmitate; alkyl myristates such as isopropyl, butyl, cetyl, 2-octyldodecyl, myristyl, or stearyl myristate; hexyl stearate; butyl stearate; isobutyl stearate; dioctyl malate; hexyl laurate; and 2-hexyldecyl laurate.

Further as additional non-limiting examples, esters of $C_4$-$C_{22}$ dicarboxylic or tricarboxylic acids and of $C_1$-$C_{22}$ alcohols, and esters of mono-, di- or tricarboxylic acids and of $C_2$-$C_{26}$ di-, tri-, tetra- or pentahydroxy alcohols may also be used.

In some embodiments, the following esters may be used: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

In some embodiments, the esters may be chosen from: ethyl, isopropyl, myristyl, cetyl, or stearyl palmitate; 2-ethylhexyl palmitate; 2-octyldecyl palmitate; alkyl myristates such as isopropyl, butyl, cetyl, or 2-octyldodecyl myristate; hexyl stearate, butyl stearate; isobutyl stearate; dioctyl malate; hexyl laurate; 2-hexyldecyl laurate; isononyl isononanoate; and cetyl octanoate.

In some embodiments, the composition may also comprise, as fatty ester, sugar esters and diesters of $C_6$-$C_{30}$, such as $C_{12}$-$C_{22}$ fatty acids. The term "sugar," as used herein, means oxygen-bearing hydrocarbon-based compounds comprising several alcohol functions, with or without aldehyde or ketone functions, and which comprise at least 4 carbon atoms. These sugars may be chosen from monosaccharides, oligosaccharides, and polysaccharides.

Non-limiting examples of suitable sugars that may be mentioned include sucrose (or saccharose), glucose, galactose, ribose, fucose, maltose, mannose, arabinose, xylose, and lactose, and derivatives thereof, for example, alkyl derivatives, such as methyl derivatives, for instance methylglucose.

The sugar esters of fatty acids may be chosen from the group comprising the esters or mixtures of esters of sugars described previously and of linear or branched, saturated or unsaturated $C_6$-$C_{30}$ fatty acids such as $C_{12}$-$C_{22}$ fatty acids. If they are unsaturated, these compounds may comprise one to three conjugated or nonconjugated carbon-carbon double bonds.

The esters according to this variant may also be chosen from mono-, di-, tri-, tetraesters and polyesters, and mixtures thereof.

These esters may be chosen, for example, from oleates, laurates, palmitates, myristates, behenates, cocoates, stearates, linoleates, linolenates, caprates and arachidonates, or mixtures thereof such as oleo-palmitate, oleo-stearate and palmito-stearate mixed esters.

In some embodiments, monoesters and diesters may be chose from sucrose, glucose or methylglucose mono- or dioleates, stearates, behenates, oleopalmitates, linoleates, linolenates and oleostearates.

An example that may be mentioned is the product sold under the name GLUCATE® DO by the company Amerchol, which is a methylglucose dioleate.

Non-limiting examples of esters or mixtures of esters of sugar and of fatty acid that may also be mentioned include:

the products sold under the names F160, F140, F110 F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name RYOTO SUGAR ESTERS, for example referenced B370 and corresponding to sucrose behenate formed from 20% monoester and 80% di- triester-polyester;

the sucrose mono-dipalmito-stearate sold by the company Goldschmidt under the name TEGOSOFT® PSE.

The non-silicone wax(es) that may be used in the anhydrous cosmetic composition (A) may be chosen from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the present disclosure include but not limited to: marine waxes, such as the product sold by the company Sophim under the reference M82, and polyethylene waxes or waxes of polyolefins in general.

The silicones that may be used in the cosmetic compositions of the present disclosure include but not limited to: volatile or nonvolatile, cyclic, linear or branched silicones, which may be unmodified or modified with organic groups, having a viscosity ranging from $5\times10^{-6}$ to 2.5 m$^2$/s at 25° C., for instance, a viscosity ranging from $1\times10^{-5}$ to 1 m$^2$/s.

The silicones that may be used in accordance with the present disclosure may be in the form of oils, waxes, resins or gums.

As non-limiting examples, the silicone is chosen from polydialkylsiloxanes such as polydimethylsiloxanes (PDMS), and organomodified polysiloxanes comprising at least one functional group chosen from poly(oxyalkylene) groups, amino groups and alkoxy groups.

The organopolysiloxanes are defined in Walter Noll's "Chemistry and Technology of Silicones" (1968) Academic Press. They can be volatile or nonvolatile.

When they are volatile, the silicones may be chosen from those having a boiling point of between 60° C. and 260° C., for instance, they may be chosen from:
(i) cyclic polydialkylsiloxanes containing from 3 to 7 such as from 4 to 5 silicon atoms. These are, for example, octamethylcyclotetrasiloxane sold, for instance, under the name VOLATILE SILICONE® 7207 by Union Carbide or SILBIONE® 70045 V 2 by Rhodia, decamethylcyclopentasiloxane sold under the name VOLATILE SILICONE® 7158 by Union Carbide, and SILBIONE® 70045 V 5 by Rhodia, and mixtures thereof.

Non-limiting mention may also be made of cyclocopolymers of the dimethylsiloxane/methylalkylsiloxane type, such as VOLATILE SILICONE® FZ 3109 sold by the company Union Carbide, of formula:

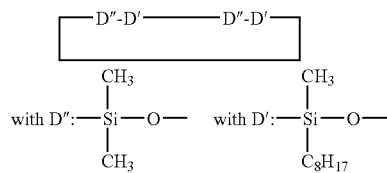

Non-limiting mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;
(ii) linear volatile polydialkylsiloxanes comprising 2 to 9 silicon atoms and having a viscosity of less than or equal to $5 \times 10^{-6}$ m$^2$/s at 25° C. A non-limiting example is decamethyltetrasiloxane sold under the name SH 200 by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

Nonvolatile polydialkylsiloxanes, polydialkylsiloxane gums and resins, polyorganosiloxanes modified with organofunctional groups above, and mixtures thereof, may be used.

These silicones may be chosen from polydialkylsiloxanes, as a non-limiting example, polydimethylsiloxanes comprising trimethylsilyl end groups. The viscosity of the silicones is measured, for example, at 25° C. according to ASTM standard 445 Appendix C.

Among these polydialkylsiloxanes, mention may be made, in a non-limiting manner, of the following commercial products:
the SILBIONE® oils of the 47 and 70 047 series or the Mirasil® oils sold by Rhodia, for instance the oil 70 047 V 500 000;
the oils of the MIRASIL® series sold by the company Rhodia;
the oils of the 200 series from the company Dow Corning, such as DC200 with a viscosity of 60 000 mm$^2$/s;
the VISCASIL® oils from General Electric and certain oils of the SF series (SF 96, SF 18) from General Electric.

Non-limiting mention may also be made of polydimethylsiloxanes comprising dimethylsilanol end groups known under the name Dimethiconol (CTFA), such as the oils of the 48 series from the company Rhodia.

In this category of polydialkylsiloxanes, mention may also be made of the products sold under the names ABIL WAX® 9800 and 9801 by the company Goldschmidt, which are poly($C_1$-$C_{20}$)dialkylsiloxanes.

The silicone gums that can be used in accordance with the present disclosure may be chosen from polydialkylsiloxanes such as polydimethylsiloxanes with high number-average molecular weight ranging from 200 000 to 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used in accordance with the present disclosure may be chosen from, in a non-limiting manner:
mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;
mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
mixtures of two PDMSs with different viscosities, for instance, of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5 \times 10^{-6}$ m$^2$/s. This product may contain 15% SE 30 gum and 85% SF 96 oil.

The organopolysiloxane resins that can be used in accordance with the present disclosure may be chosen from crosslinked siloxane systems containing the following units:

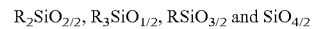

wherein R is chosen from hydrocarbon-based groups containing 1 to 16 carbon atoms. As a non-limiting example, R is chosen from $C_1$-$C_4$ lower alkyl radicals such as methyl. Among these resins, non-limiting mention may be made of the product sold under the name Dow Corning 593 or those sold under the names SILICONE FLUID SS 4230 and SS 4267 by the company General Electric, which are silicones of dimethyl/trimethyl siloxane structure.

Non-limiting mention may also be made of the trimethyl siloxysilicate type resins sold under the names X22-4914, X21-5034 and X21-5037 by the company Shin-Etsu.

The organomodified silicones that can be used in accordance with the present disclosure may be chosen from the silicones as defined above and comprising in their structure at least one organofunctional group attached via a hydrocarbon-based radical.

Besides the silicones described above, the organomodified silicones may be chosen from polydiarylsiloxanes, such as polydiphenylsiloxanes, and polyalkylarylsiloxanes functionalized with the organofunctional groups mentioned previously.

The polyalkylarylsiloxanes may be chosen from linear and/or branched polydimethyl/methylphenylsiloxanes and polydimethyl/diphenylsiloxanes with a viscosity of from $1 \times 10^{-5}$ to $5 \times 10^{-2}$ m$^2$/s at 25° C.

Among these polyalkylarylsiloxanes, examples that may be mentioned include but not limited to the products sold under the following names:
the SILBIONE® oils of the 70 641 series from Rhodia;
the oils of the RHODOURSIL® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold under the name GP 4 SILICONE FLUID and GP 7100 by the company Genesee, or the products sold under the names Q2 8220 and Dow Corning 929 or 939 by the company Dow Corning. The substituted amine groups may be chosen from $C_1$-$C_4$ aminoalkyl groups;

alkoxylated groups such as the product sold under the name SILICONE COPOLYMER F-755 by SWS Silicones, and ABIL WAX® 2428, 2434 and 2440 by the company Goldschmidt.

In some embodiments, the fatty substances do not comprise any oxyalkylene units or any glycerolated units.

In some embodiments, the fatty substance is a compound that is liquid at a temperature of 25° C. and at atmospheric pressure.

In some embodiments, the fatty substances are not fatty acids.

The fatty substances may be chosen from $C_6$-$C_{16}$ lower alkanes, non-silicone oils of mineral, plant or synthetic origin, fatty alcohols, esters of a fatty acid, esters of a fatty alcohol, and silicones.

According to one embodiment, the at least one fatty substance is chosen from liquid petroleum jelly, polydecenes, fatty acid and/or fatty alcohol esters, liquid esters.

In some embodiments, the at least one fatty substance of the composition according to the present disclosure is chosen from non-silicone oils.

In some embodiments, composition (A) according to the present disclosure comprises the at least one fatty substance in an amount ranging from 25% to 80% by weight, relative to the total weight of the composition.

In some embodiments, in the implementation of the lightening processes according to the present disclosure, the anhydrous cosmetic composition (A) comprised of at least one fatty substance in an amount ranging from 10% to 99% by weight, for instance, ranging from 20% to 90% by weight such as ranging from 25% to 80% by weight relative to the weight of the anhydrous composition.

In some embodiments, in the implementation of the dyeing processes according to the present disclosure, composition (A) comprised of at least 25% of at least one fatty substance. For example, the concentration of at least one fatty substance ranges from 25% to 80%, for instance, from 25% to 65% such as from 30% to 55% of the total weight of the composition.

The anhydrous cosmetic composition (A) also comprises at least one surfactant.

In some embodiments, the at least one surfactant is chosen from nonionic surfactants and anionic surfactants.

The anionic surfactants may be chosen from the salts (such as alkali metal salts, for instance, sodium salts, ammonium salts, amino salts such as amino alcohol salts or alkaline-earth metal salts such as magnesium salts) of the following compounds:

alkyl sulfates, alkyl ether sulfates, alkylamido ether sulfates, alkylaryl polyether sulfates, monoglyceride sulfates;

alkylsulfonates, alkylamidesulfonates, alkylarylsulfonates, α-olefin sulfonates, paraffin sulfonates;

alkyl phosphates, alkyl ether phosphates;

alkylsulfosuccinates, alkyl ether sulfosuccinates, alkylamidesulfosuccinates; alkylsulfosuccinamates;

alkylsulfoacetates;

acylsarcosinates; acylisethionates and N-acyltaurates;

salts of fatty acids such as oleic acid, ricinoleic acid, palmitic acid or stearic acid, coconut oil acid or hydrogenated coconut oil acid;

alkyl-D-galactoside uronic acid salts;

acyllactylates;

salts of polyoxyalkylenated alkyl ether carboxylic acids, of polyoxyalkylenated alkylaryl ether carboxylic acids or of polyoxyalkylenated alkylamido ether carboxylic acids, for example, those comprising from 2 to 50 ethylene oxide groups;

and mixtures thereof.

The alkyl or acyl radical of these various compounds may contain from 6 to 24 carbon atoms such as from 8 to 24 carbon atoms, and the aryl radical may be chosen from phenyl and benzyl groups.

The nonionic surfactants may be chosen from monooxyalkylenated or polyoxyalkylenated, monoglycerolated or polyglycerolated nonionic surfactants. The oxyalkylene units may be chosen from oxyethylene and oxypropylene units, or a combination thereof, such as oxyethylene units.

Non-limiting examples of oxyalkylenated nonionic surfactants that may be mentioned include:

oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyethylenated esters of saturated or unsaturated, linear or branched, $C_8$-$C_{30}$ acids and of sorbitol, saturated or unsaturated, oxyethylenated plant oils, condensates of ethylene oxide and/or of propylene oxide, inter alia, or mixtures thereof.

The surfactants may contain a number of moles of ethylene oxide and/or of propylene oxide ranging from 1 to 100 moles such as ranging from 2 to 50 moles. In some embodiments, the nonionic surfactants do not comprise any oxypropylene units.

In accordance with one embodiment of the present disclosure, the oxyalkylenated nonionic surfactants are chosen from oxyethylenated $C_8$-$C_{30}$ alcohols, polyoxyethylenated linear or branched, saturated or unsaturated $C_8$-$C_{30}$ acid esters, and polyoxyethylenated sorbitol esters.

As non-limiting examples of monoglycerolated or polyglycerolated nonionic surfactants, monoglycerolated or polyglycerolated $C_8$-$C_{40}$ alcohols may be used.

In some embodiments, the monoglycerolated or polyglycerolated $C_8$-$C_{40}$ alcohols correspond to the following formula:

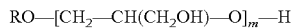

RO—[CH$_2$—CH(CH$_2$OH)—O]$_m$—H wherein R is chosen from linear or branched $C_8$-$C_{40}$ alkyl or alkenyl radicals, such as $C_8$-$C_{30}$ alkyl or alkenyl radicals, and m is chosen from a number ranging from 1 to 30, such as from 1 to 10.

As examples of compounds that may be suitable in the context of the present disclosure, non-limiting mention may be made of lauryl alcohol comprising 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may be chosen from a mixture of alcohols in the same way that the value of m refers to a statistical value, which means that, in a commercial product, several species of polyglycerolated fatty alcohol may coexist in the form of a mixture.

In some embodiments, the monoglycerolated or polyglycerolated alcohols may be chosen from the $C_8$/$C_{10}$ alcohol containing 1 mol of glycerol, the $C_{10}$/$C_{12}$ alcohol containing 1 mol of glycerol, and the $C_{12}$ alcohol containing 1.5 mol of glycerol.

In some embodiments, the at least one surfactant present in the composition of the present disclosure is a nonionic surfactant.

In some embodiments, the anhydrous composition (A) comprised of at least one surfactant content in an amount ranging from 0.1% to 50% by weight, such as from 0.5% to 30% by weight, relative to the weight of the anhydrous composition.

The anhydrous composition (A) may further comprise at least one adjuvant chosen from the those conventionally used in hair dye or hair lightening compositions, such as anionic, cationic, nonionic, amphoteric or zwitterionic polymers or mixtures thereof; mineral thickeners, for example, fillers such as clays, talc; organic thickeners with, for example, anionic, cationic, nonionic, and amphoteric polymeric associative thickeners; anti-oxidants; penetrants; sequestrants; fragrances; dispersants; film-forming agents; ceramides; preserving agents; opacifiers.

The adjuvants may be present in an amount, for each of them, ranging from 0.01% to 20% by weight relative to the weight of composition (A).

In some embodiments, the composition may comprise at least one mineral thickeners chosen from organophilic clays and fumed silicas, or mixtures thereof.

The organophilic clay may be chosen from montmorillonite, bentonite, hectorite, attapulgite and sepiolite, and mixtures thereof. For instance, the clay is chosen from bentonite and hectorite.

These clays may be modified with a chemical compound chosen from quaternary amines, tertiary amines, amine acetates, imidazolines, amine soaps, fatty sulfates, alkyl aryl sulfonates and amine oxides, and mixtures thereof.

Organophilic clays that may be mentioned include quaternium-18 bentonites such as those sold under the names BENTONE 3, BENTONE 38 and BENTONE 38V by the company Rheox, TIXOGEL VP by the company United Catalyst, CLAYTONE 34, CLAYTONE 40 and CLAYTONE XL by the company Southern Clay; stearalkonium bentonites such as those sold under the names BENTONE 27 by the company Rheox, TIXOGEL LG by the company United Catalyst and CLAYTONE AF and CLAYTONE APA by the company Southern Clay; quaternium-18/benzalkonium bentonites such as those sold under the names CLAYTONE HT and CLAYTONE PS by the company Southern Clay.

The fumed silicas may be obtained by high-temperature hydrolysis of a volatile silicon compound in an oxhydric flame, producing a finely divided silica. This process makes it possible to obtain, for instance, hydrophilic silicas having a large number of silanol groups at their surface. Such hydrophilic silicas are sold, for example, under the names AEROSIL 130®, AEROSIL 200®, AEROSIL 255®, AEROSIL 300® and AEROSIL 380® by the company Degussa, and CAB-O-SIL HS-5®, CAB-O-SIL EH-5®, CAB-O-SIL LM-130®, CAB-O-SIL MS-55® and CAB-O-SIL M-5® by the company Cabot.

It is possible to chemically modify the surface of the silica via chemical reaction in order to reduce the number of silanol groups. Silanol groups may be substituted with, for instance, hydrophobic groups, and a hydrophobic silica is then obtained.

The hydrophobic groups may be chosen from:
trimethylsiloxyl groups, which may be obtained by treating fumed silica in the presence of hexamethyldisilazane. Silicas thus treated are known as "Silica silylate" according to the CTFA (6th edition, 1995). They are sold, for example, under the references AEROSIL R812® by the company Degussa and CAB-O-SIL TS-530® by the company Cabot.
dimethylsilyloxyl or polydimethylsiloxane groups, which may be obtained by treating fumed silica in the presence of polydimethylsiloxane or dimethyldichiorosilane. Silicas thus treated are known as "Silica dimethyl silylate" according to the CTFA (6th edition, 1995). They are sold, for example, under the references AEROSIL R972® and AEROSIL R974® by the company Degussa, and CAB-O-SIL TS-610® and CAB-O-SIL TS-720® by the company Cabot.

The fumed silica may have a particle size that may be nanometric to micrometric, for example ranging from about 5 to 200 nanometers.

In some embodiments, the composition comprises a hectorite, an organomodified bentonite or a fumed silica, which is optionally modified.

When it is present, the mineral thickener may be present in an amount ranging from 1% to 30% by weight relative to the weight of the composition.

The composition may also comprise at least one organic thickener.

These thickeners may be chosen from fatty acid amides (coconut acid diethanolamide or monoethanolamide, oxyethylenated alkyl ether carboxylic acid monoethanolamide), polymeric thickeners such as cellulose-based thickeners (hydroxyethylcellulose, hydroxypropylcellulose, carboxymethylcellulose), guar gum and derivatives thereof (hydroxypropylguar), gums of microbial origin (xanthan gum, scleroglucan gum), crosslinked homopolymers of acrylic acid or of acrylamidopropanesulfonic acid, and associative polymers (polymers comprising hydrophilic zones and hydrophobic zones with a fatty chain (alkyl or alkenyl containing at least 10 carbon atoms) capable, in an aqueous medium, of reversibly associating with each other or with other molecules).

In some embodiments, the organic thickener is chosen from cellulose-based thickeners (hydroxyethylcellulose, hydroxypropylcellulose, carboxymethylcellulose), guar gum and derivatives thereof (hydroxypropylguar), gums of microbial origin (xanthan gum, scleroglucan gum), and crosslinked homopolymers of acrylic acid or of acrylamidopropane-sulfonic acid. As a non-limiting example, the organic thickener is chosen from cellulose-based thickeners such as hydroxyethylcellulose.

The content of organic thickener(s), if they are present, usually ranges from 0.01% to 20% by weight such as from 0.1% to 5% by weight relative to the weight of the composition.

In some embodiments, the composition (A) is in the form of a gel or a cream.

In the case of performing a lightening process, composition (B) does not comprise any direct dye or oxidation dye precursor (bases and couplers), or else, if they are present, their total content does not exceed 0.005% by weight relative to the weight of composition (B); for example, the lightening process is performed without oxidation base, or coupler, or direct dye.

The dyeing process according to the present disclosure is performed in the presence of a cosmetic composition (B) comprising at least one oxidation dye and/or at least one direct dye.

The at least one oxidation dye may be chosen from oxidation bases optionally combined with at least one couplers.

The oxidation bases are chosen, for example, from para-phenylenediamines, bis(phenyl)alkylenediamines, para-aminophenols, ortho-aminophenols and heterocyclic bases, and the addition salts thereof.

The para-phenylenediamines may be chosen from, as non-limiting examples, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(p-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(p-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxy-propyl)-para-phenylenediamine, N-(4'-aminophenyl)-para-phenylenediamine, N-phenyl-para-phenylenediamine, 2-β-hydroxyethyloxy-para-phenylenediamine, 2-β-acetylamino-ethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and 3-hydroxy-1-(4'-aminophenyl) pyrrolidine, and the addition salts thereof with an acid.

In some embodiments, the para-phenylenediamines are chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, and 2-β-acetylaminoethyloxy-para-phenylenediamine, and the addition salts thereof with an acid.

In some embodiments, bis(phenyl)alkylenediamines are chosen from, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, and 1,8-bis(2,5-diamino-phenoxy)-3,6-dioxaoctane, and the addition salts thereof.

Para-aminophenols may be chosen from, for example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and 4-amino-2-fluorophenol, and the addition salts thereof with an acid.

Ortho-aminophenols may be chosen from, for example, 2-aminophenol, 2-amino-5-methylphenol, 2-amino-6-methylphenol, and 5-acetamido-2-aminophenol, and the addition salts thereof.

The heterocyclic bases may be chosen from, for example, pyridine derivatives, pyrimidine derivatives, and pyrazole derivatives.

The pyridine derivatives include but are not limited to, the compounds described, for example, in United Kingdom Patent Nos. GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that may be useful in the dyeing process according to the present disclosure include but not limited to: 3-aminopyrazolo[1,5-a]-pyridine oxidation bases or addition salts thereof described, for example, in French Patent Application No. FR 2 801 308. Non-limiting examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5morpholin-4-yl-pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, and 3-aminopyrazolo[1,5-a]pyridin-7-ol, and the addition salts thereof.

The pyrimidine derivatives that may be mentioned include but not limited to, the compounds described, for example, in German Patent No. DE 2 359 399; Japanese Patent No. 88-169 571; Japanese Patent No. 05-63124; European Patent No. EP 0 770 375 or International Patent Application Publication No. WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned include but are not limited to, the compounds described in German Patent Nos. DE 3 843 892 and DE 4 133 957, and International Patent Application Publication Nos. WO 94/08969 and WO 94/08970, French Patent No. A-2 733 749 and German Patent Publication No. DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(3-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, and 3,5-diamino-4-(β-hydroxyethyl)amino-1-methylpyrazole, and the addition salts thereof. 4,5-Diamino-1-(β-methoxyethyl)pyrazole may also be used.

In some embodiments, a 4,5-diaminopyrazole may be used, or 4,5-diamino-1(β-hydroxyethyl)pyrazole and/or a salt thereof may be used.

Pyrazole derivatives that may be used include but not limited to, diamino-N,N-dihydropyrazolopyrazolones, such as those described in French Patent Application No. FR-A-2 886 136, and such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, and 2,3-diamino-6-hydroxy-6,7-dihydro-1H,5H-pyrazolo-[1,2-a]pyrazol-1-one.

As a non-limiting example, 2,3-Diamino-6,7-dihydro-1H,5H-pyrazolo[1,2-a]pyrazol-1-one and/or a salt thereof may be used.

Further as a non-limiting example, 4,5-Diamino-1-(β-hydroxyethyl)pyrazole and/or 2,3-diamino-6,7-dihydro-1H,5H-pyrazolo[1,2-a]pyrazol-1-one and/or a salt thereof may be used as heterocyclic bases.

The cosmetic composition (B) used in the dyeing process according to the present disclosure may optionally comprise at least one coupler chosen from those conventionally used in the dyeing of keratin fibers.

In some embodiments, the at least one coupler is chosen from meta-phenylenediamines, meta-aminophenols, meta-diphenols, naphthalene-based couplers, and heterocyclic couplers, and also the addition salts thereof.

Non-limiting mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methyl-indole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazo-5-one, 1-phenyl-3-methylpyrazol-5-one, 2,6-dimethylpyrazolo[1,5-b]-1,2,4-triazole, 2,6-dimethyl[3,2-c]-1,2,4-triazole, and 6-methylpyrazolo[1,5-a]benzimidazole, the addition salts thereof with an acid, and mixtures thereof.

In some embodiments, the addition salts of the oxidation bases and couplers that may be used in the context of the present disclosure may be chosen from the addition salts with an acid such as the hydrochlorides, hydrobromides, sulfates, citrates, succinates, tartrates, lactates, tosylates, benzenesulfonates, phosphates, and acetates.

The at least one oxidation may be present in an amount ranging from 0.0001% to 10% by weight relative to the total weight of the composition, for example, from 0.005% to 5% by weight relative to the total weight of the composition.

The content of at least one coupler, if it is present, may be present in an amount ranging from 0.0001% to 10% by weight relative to the total weight of the composition, for example, from 0.005% to 5% by weight relative to the total weight of the cosmetic composition (B).

In some embodiments, the direct dyes may be chosen from ionic and nonionic species, such as cationic or nonionic species.

Non-limiting examples of suitable direct dyes that may be mentioned include azo; methine; carbonyl; azine; nitro(hetero)aryl; tri(hetero)arylmethane; porphyrin; phthalocyanin direct dyes, and natural direct dyes, alone or as mixtures.

In some embodiments, the azo dyes comprise an —N═N— function, the two nitrogen atoms of which are not simultaneously engaged in a ring. However, it is not excluded for one of the two nitrogen atoms of the sequence —N═N— to be engaged in a ring.

The dyes of the methine family may be chosen from compounds comprising at least one sequence chosen from >C═C< and —N═C<, the two atoms of which are not simultaneously engaged in a ring. However, one of the nitrogen or carbon atoms of the sequences may be engaged in a ring. As non-limiting examples, the dyes of this family may be derived from compounds of the type such as methines, azomethines, mono- and diarylmethanes, indoamines (or diphenylamines), indophenols, indoanilines, carbocyanins, azacarbocyanins and isomers thereof, diazacarbocyanins and isomers thereof, tetraazacarbocyanins, and hemicyanins.

The dyes of the carbonyl family include but not limited to, dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole, and coumarin.

As regards the dyes of the cyclic azine family, non-limiting mention may be made of azine, xanthene, thioxanthene, fluorindine, acridine, (di)oxazine, (di)thiazine and pyronin.

The nitro(hetero)aromatic dyes may be chosen from, for example, nitrobenzene and nitropyridine direct dyes.

As regards the dyes of porphyrin or phthalocyanin type, it is possible to use cationic or noncationic compounds, optionally comprising at least one metal or metal ion, for instance alkali metals, alkaline-earth metals, zinc and silicon.

Non-limiting examples of suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinine, such as anthraquinone, naphthoquinone or benzoquinone direct dyes; azine; xanthene; triarylmethane; indoamine; indigoid; phthalocyanin direct dyes, porphyrins, and natural direct dyes, alone or as mixtures.

These dyes may be monochromophoric dyes (i.e. comprising only one dye) or polychromophoric, such as di- or trichromophoric; the chromophores possibly being identical or different, and from the same chemical family or otherwise. A polychromophoric dye comprises several radicals each derived from a molecule that absorbs in the visible region ranging from 400 and 800 nm. Furthermore, this absorbance of the dye does not require any prior oxidation thereof, or combination with any other chemical species.

In the case of polychromophoric dyes, the chromophores may be connected together by means of at least one linker, which may be cationic or noncationic.

As non-limiting examples, the at least one linker may be chosen from linear, branched or cyclic $C_1$-$C_{20}$ alkyl chains, optionally interrupted with at least one heteroatom (such as nitrogen or oxygen) and/or with at least one group comprising such an atom ($CO$, $SO_2$), optionally interrupted with at least one heterocycle that may or may not be fused to a phenyl nucleus and comprising at least one quaternized nitrogen atom engaged in said ring and optionally at least one other heteroatom (such as oxygen, nitrogen or sulfur), optionally interrupted with at least one substituted or unsubstituted phenyl or naphthyl group, optionally at least one quaternary ammonium group substituted with two optionally substituted $C_1$-$C_{15}$ alkyl groups; the linker not comprising any nitro, nitroso or peroxy groups.

If the heterocycles or aromatic nuclei are substituted, they may be substituted, for example, with at least one $C_1$-$C_8$ alkyl radical optionally substituted with a hydroxyl, $C_1$-$C_2$ alkoxy, $C_2$-$C_4$ hydroxyalkoxy, acetylamino, or amino group substituted with one or two $C_1$-$C_4$ alkyl radicals, optionally bearing at least one hydroxyl group, or the two radicals possibly forming, with the nitrogen atom to which they are attached, a 5- or 6-membered heterocycle optionally comprising another heteroatom identical to or different than nitrogen; a halogen atom; a hydroxyl group; a $C_1$-$C_2$ alkoxy radical; a $C_2$-$C_4$ hydroxyalkoxy radical; an amino radical; an amino radical substituted with one or two identical or different $C_1$-$C_4$ alkyl radicals optionally bearing at least one hydroxyl group.

Among the benzenic direct dyes that may be used according to the present disclosure, mention may be made in a non-limiting manner of the following compounds:
1,4-diamino-2-nitrobenzene,
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo, azomethine, methine and tetraazapentamethine direct dyes that may be used according to the present disclosure, non-limiting mention may be made of the cationic dyes described in International Patent Application Publication Nos. WO 95/15144, WO 95/01772 and European Patent No. 714 954; French Patent Application Nos. FR 2 189 006, FR 2 285 851, FR 2 140 205, European Patent Application Publication Nos. 1 378 544 and EP 1 674 073.

Thus, non-limiting mention may be made of the following dyes of formulae (I) to (IV), such as the compounds of formulae (I) and (III):

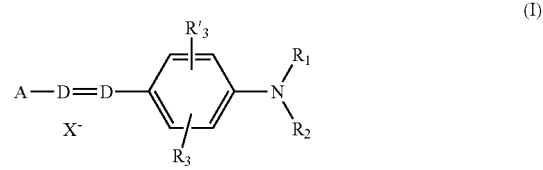

(I)

wherein:
D is chosen from a nitrogen atom and a —CH group,
$R_1$ and $R_2$, which may be identical or different, are chosen from a hydrogen atom; $C_1$-$C_4$ alkyl radicals which may be substituted with a —CN, —OH or —NH$_2$ radical, or form, with a carbon atom of the benzene ring, a heterocycle optionally containing oxygen or nitrogen, which may be substituted with at least one $C_1$-$C_4$ alkyl radicals; and a 4'-aminophenyl radical,
$R_3$ and $R'_3$, which may be identical or different, are chosen from a hydrogen atom, halogen atoms chosen from chlorine, bromine, iodine, and fluorine, a cyano, $C_1$-$C_4$ alkyls, $C_1$-$C_4$ alkoxy radicals, and a acetyloxy radical,
$X^-$ is chosen from anions, for example, chosen from chloride, methyl sulphate, and acetate,
A is chosen from a group chosen from structures A1 to A18, such as A1, A4, A7, A13, and A18, below:

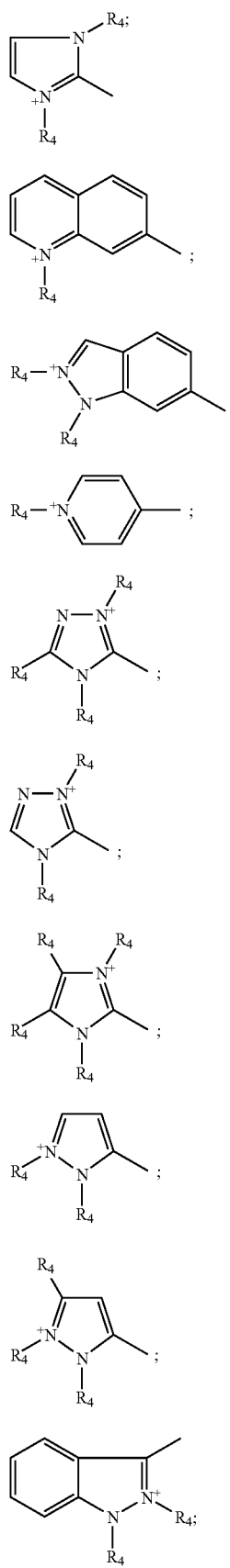
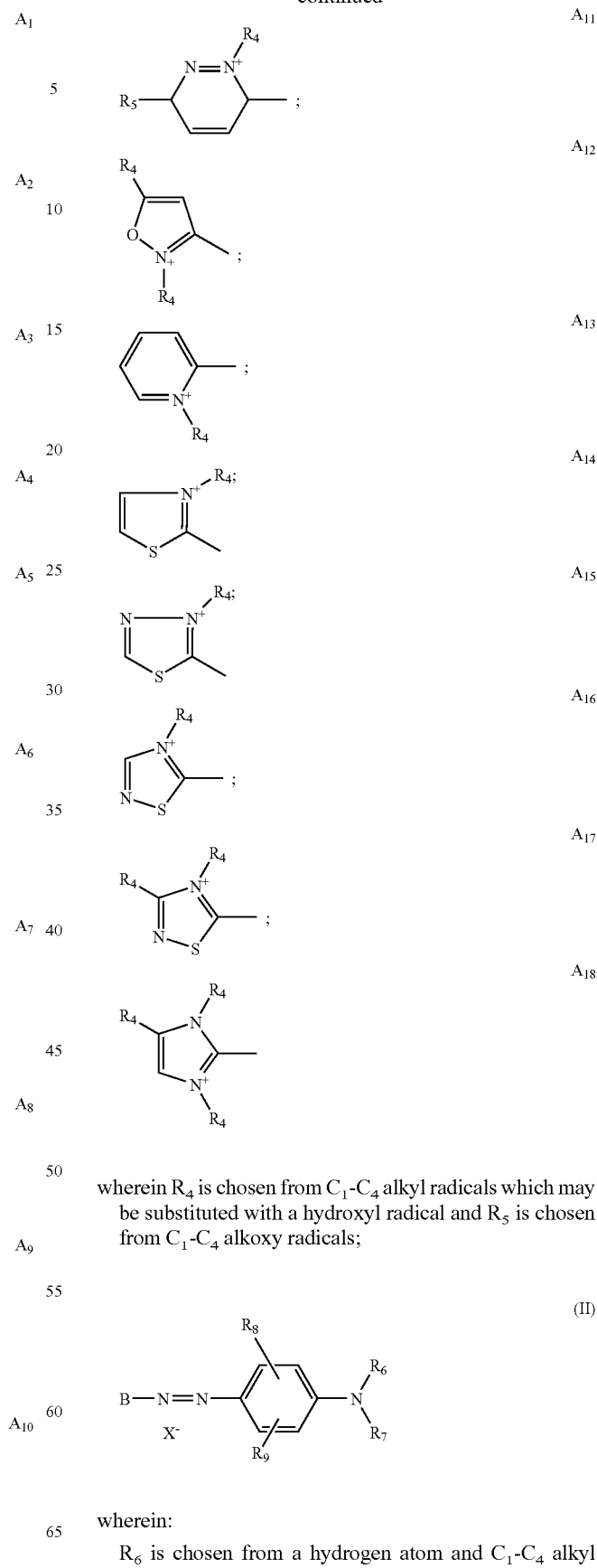
wherein $R_4$ is chosen from $C_1$-$C_4$ alkyl radicals which may be substituted with a hydroxyl radical and $R_5$ is chosen from $C_1$-$C_4$ alkoxy radicals;
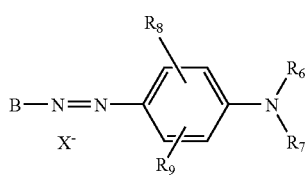
(II)
wherein:
$R_6$ is chosen from a hydrogen atom and $C_1$-$C_4$ alkyl radicals, $R_7$ is chosen from a hydrogen atom, alkyl radicals which may be substituted with a —CN radical or with an amino group, a 4'-aminophenyl radical, or forms with $R_6$ a heterocycle optionally containing oxygen and/or nitrogen, which may be substituted with a $C_1$-$C_4$ alkyl radical, $R_8$ and $R_9$, which may be identical or different, are chosen from a hydrogen atom, halogen atoms such as bromine, chlorine, iodine or fluorine, $C_1$-$C_4$ alkyl radicals, $C_1$-$C_4$ alkoxy radicals, and a —CN radical, $X^-$ is chosen from anions such as chosen from chloride, methyl sulfate, and acetate, B is chosen from a group chosen from structures $B_1$ to $B_6$ below:

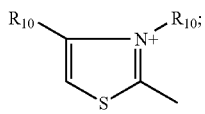

B1

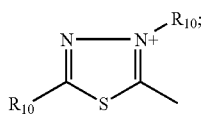

B2

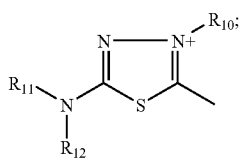

B3

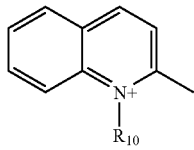

B4

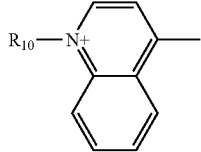

B5

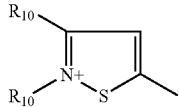

B6 wherein $R_{10}$ is chosen from $C_1$-$C_4$ alkyl radicals, $R_{11}$ and $R_{12}$, which may be identical or different, are chose from a hydrogen atom and $C_1$-$C_4$ alkyl radicals;

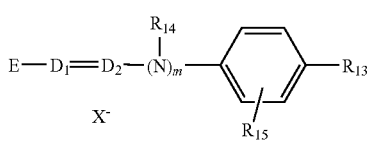

(III)

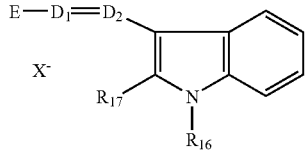

(iii')

wherein:
$R_{13}$ is chosen from a hydrogen atom, $C_1$-$C_4$ alkoxy radicals, halogen atoms such as bromine, chlorine, iodine or fluorine, and amino radicals, $R_{14}$ is chosen from a hydrogen atom, $C_1$-$C_4$ alkyl radicals or forms, with a carbon atom of the benzene ring, a heterocycle optionally containing oxygen and/or substituted with at least one $C_1$-$C_4$ alkyl group, $R_{15}$ is chosen from a hydrogen atom and halogen atoms such as bromine, chlorine, iodine, or fluorine, $R_{16}$ and $R_{17}$, which may be identical or different, are chosen from a hydrogen atom and $C_1$-$C_4$ alkyl radicals, $D_1$ and $D_2$, which may be identical or different, are chosen from a hydrogen atom and a —CH group, m is chosen from 0 and 1, for example, m=1, with proviso that when $R_{13}$ is chosen from unsubstituted amino groups, then $D_1$ and $D_2$ are chosen from a —CH group and m=0, $X^-$ is chosen from anions such as chosen from chloride, methyl sulfate, and acetate, E is a group chosen from structures E1 to E8, for instance, E1, E2 and E7, below:

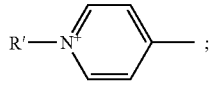

E1

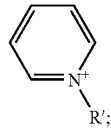

E2

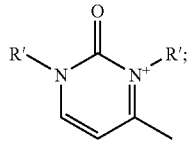

E3

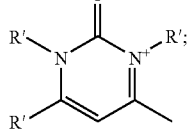

E4

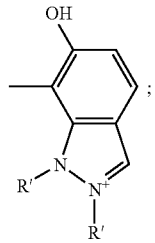

E5

-continued

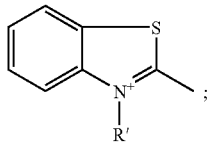 E6

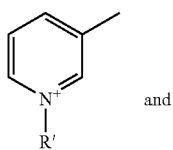 E7 and

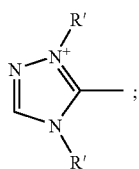 E8 wherein R' is chosen from $C_1$-$C_4$ alkyl radicals;
when m=0 and $D_1$ is a nitrogen atom, then E may be chosen from a group of structure E9 below:

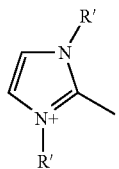 E9 wherein R' is chosen from $C_1$-$C_4$ alkyl radicals.

$$G-N=N-J \quad (IV)$$

wherein:
the symbol G is a group chosen from the structures $G_1$ to $G_3$ below:

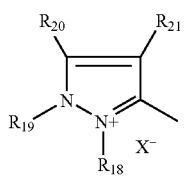 $G_1$

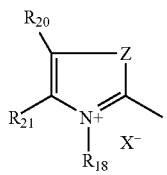 $G_2$

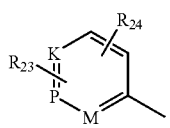 $G_3$ wherein structures $G_1$ to $G_3$:
- $R_{18}$ is chosen from $C_1$-$C_4$ alkyl radicals, phenyl radicals which may be substituted with a $C_1$-$C_4$ alkyl radical, and halogen atoms chosen from chlorine, bromine, iodine and fluorine;
- $R_{19}$ is chosen from $C_1$-$C_4$ alkyl radicals and phenyl radicals;
- $R_{20}$ and $R_{21}$, which may be identical or different, are chosen from $C_1$-$C_4$ alkyl radicals and phenyl radicals, or form together in $G_1$ a benzene ring substituted with at least one $C_1$-$C_4$ alkyl, $C_1$-$C_4$ alkoxy, or $NO_2$ radical, or form together in $G_2$ a benzene ring optionally substituted with at least one $C_1$-$C_4$ alkyl, $C_1$-$C_4$ alkoxy, or $NO_2$ radical;
- $R_{20}$ may be a hydrogen atom;
- Z may be chosen from oxygen atom, sulfur atom, and a group —$NR_{19}$;
- M is chosen from —CH, —CR (R is chosen from $C_1$-$C_4$ alkyls), and —$NR_{22}(X^-)_r$;
- K is chosen from —CH, —CR (R is chosen from $C_1$-$C_4$ alkyls), and —$NR_{22}(X^-)_r$;
- P is chosen from —CH, —CR (R is chosen from $C_1$-$C_4$ alkyls), and —$NR_{22}(X^-)_r$;
- r is chosen from 0 and 1;
- $R_{22}$ is chosen from an $O^-$ atom, $C_1$-$C_4$ alkoxy radicals, $C_1$-$C_4$ alkyl radicals;
- $R_{23}$ and $R_{24}$, which may be identical or different, are chosen from hydrogen atom, halogen atoms chosen from chlorine, bromine, iodine, and fluorine, $C_1$-$C_4$ alkyl radicals, $C_1$-$C_4$ alkoxy radicals, and an —$NO_2$ radical;
- $X^-$ is chosen from anions such as chosen from chloride, iodide, methyl sulfate, ethyl sulfate, acetate, and perchlorate;

with the proviso that,
if $R_{22}$ is $O^-$, then r is zero;
if K or P or M is chosen from —N—($C_1$-$C_4$)alkyl $X^-$, then $R_{23}$ or $R_{24}$ may not be a hydrogen atom;
if K is chosen from —$NR_{22}(X^-)_r$, then M=P and are chose from —CH and —CR;
if M is chosen from —$NR_{22}(X^-)_r$, then K=P and are chosen from —CH and —CR;
if P is chosen from —$NR_{22}(X^-)_r$, then K=M and are chose from —CH or —CR;
if Z is chosen from a sulfur atom with $R_{21}$ being chosen from $C_1$-$C_4$ alkyl, then $R_{20}$ is not a hydrogen atom;
if Z is chosen from —$NR_{22}$ with $R_{19}$ being chosen from $C_1$-$C_4$ alkyl, then at least one of the radicals $R_{18}$, $R_{20}$, and $R_{21}$ of the group of structure $G_2$ is not a $C_1$-$C_4$ alkyl radical;
the symbol J is chosen from:
(a) a group of structure $J_1$ below:

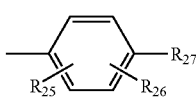 $J_1$ wherein structure $J_1$:
- $R_{25}$ is chosen from a hydrogen atom, halogen atoms chosen from chlorine, bromine, iodine, and fluorine, $C_1$-$C_4$ alkyl radicals, $C_1$-$C_4$ alkoxy radicals, —OH, —$NO_2$, —$NHR_{28}$, —$NR_{29}R_{30}$, and $C_1$-$C_4$ —NH-COalkyl radicals, or forms with $R_{26}$ a 5- or 6-membered ring optionally comprising at least one heteroatom chosen from nitrogen, oxygen, and sulfur;

$R_{26}$ is chosen from a hydrogen atom, halogen atoms chosen from chlorine, bromine, iodine, and fluorine, $C_1$-$C_4$ alkyl radicals, and $C_1$-$C_4$ alkoxy radicals, or forms with $R_{27}$ or $R_{28}$ a 5- or 6-membered ring optionally comprising at least one heteroatom chosen from nitrogen, oxygen, and sulfur;

$R_{27}$ is chosen from a hydrogen atom, an —OH radical, —$NHR_{28}$ radicals, and —$NR_{29}R_{30}$ radicals;

$R_{28}$ is chosen from a hydrogen atom, $C_1$-$C_4$ alkyl radicals, $C_1$-$C_4$ monohydroxyalkyl radicals, $C_2$-$C_4$ polyhydroxyalkyl radicals, and phenyl radicals;

$R_{29}$ and $R_{30}$, which may be identical or different, are chosen from $C_1$-$C_4$ alkyl radicals, $C_1$-$C_4$ monohydroxyalkyl radicals, and $C_2$-$C_4$ polyhydroxyalkyl radicals;

(b) a 5- or 6-membered nitrogenous heterocyclic group, which may contain other heteroatoms and/or carbonyl groups and may be substituted with at least one $C_1$-$C_4$ alkyl, amino, or phenyl radical; for example, a group of structure $J_2$ below:

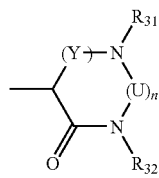

wherein structure $J_2$:

$R_{31}$ and $R_{32}$, which may be identical or different, are chosen from a hydrogen atom, $C_1$-$C_4$ alkyl radicals, and phenyl radicals;

Y is chosen from a —CO— radical and a

radical;

n is chosen from 0 and 1, with a proviso that when n is 1, U is a —CO— radical.

In structures (I) to (IV) defined above, the $C_1$-$C_4$ alkyl or alkoxy group may be chosen from methyl, ethyl, butyl, methoxy, and ethoxy.

As non-limiting examples, the compounds of formulae (I) and (III) may be chosen from:

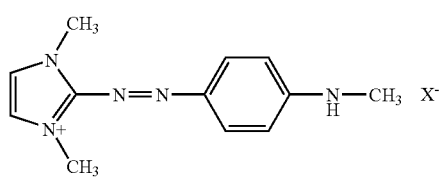

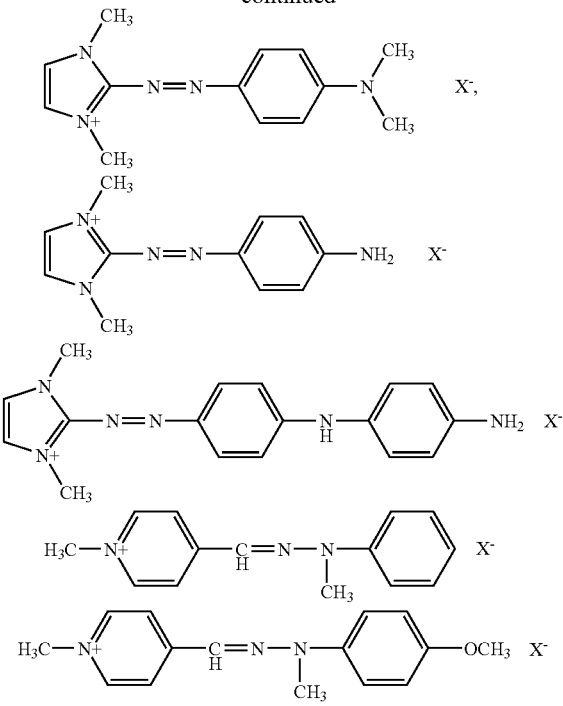

In some embodiments, the azo direct dyes may be chosen from the following dyes, described in the Color Index International, 3rd edition:

Disperse Red 17
Basic Red 22
Basic Red 76
Basic Yellow 57
Basic Brown 16
Basic Brown 17
Disperse Black 9.

Non-limiting mention may also be made of 1-(4'-aminodiphenylazo)-2-methyl-4-bis(β-hydroxyethyl)aminobenzene.

In some embodiments, the quinone direct dyes may be chosen from the following dyes:

Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99 and also the following compounds:

1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

In some embodiments, the azine dyes may be chosen from the following compounds:

Basic Blue 17

Basic Red 2.

The triarylmethane dyes that may be used according to the present disclosure include but not limited to the following compounds:

Basic Green 1

Basic Violet 3

Basic Violet 14

Basic Blue 7

Basic Blue 26.

The indoamine dyes that may be used according to the present disclosure include but not limited to the following compounds:

2-β-hydroxyethylamino-5-[bis(β-4'-hydroxyethyl)amino]anilino-1,4-benzoquinone

2-β-hydroxyethylamino-5-(2'-methoxy-4'-amino)anilino-1,4-benzoquinone

3-N-(2'-chloro-4'-hydroxy)phenylacetylamino-6-methoxy-1,4-benzoquinone imine

3-N-(3'-chloro-4'-methylamino)phenylureido-6-methyl-1,4-benzoquinone imine

3-[4'-N-(ethyl,carbamylmethyl)amino]phenylureido-6-methyl-1,4-benzoquinone imine.

Among the dyes of tetraazapentamethine type that may be used according to the present disclosure, non-limiting mention may be made of the following compounds given in the table below, An being defined as previously:

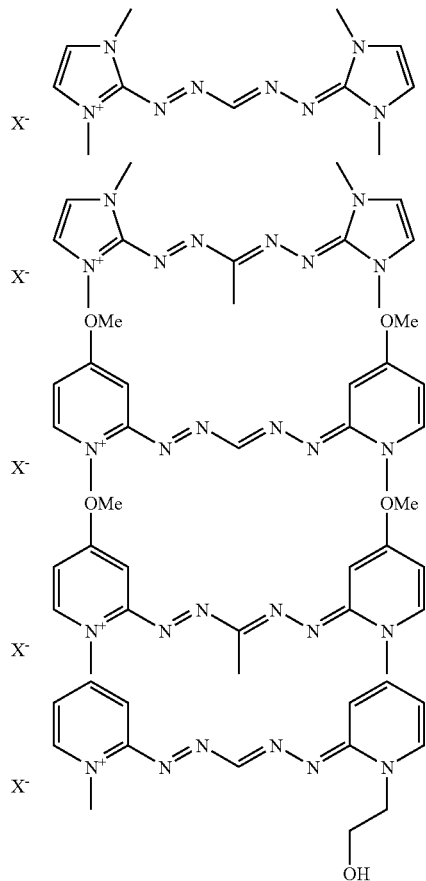

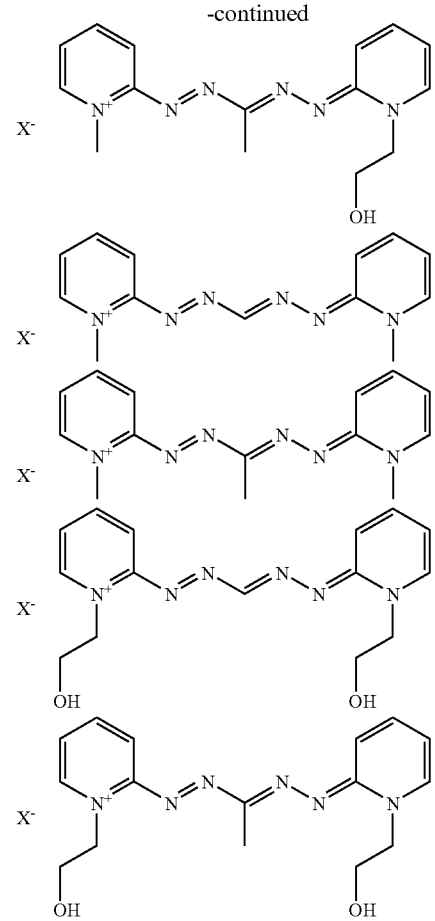

$X^-$ is chosen from anions, for instance, $X^-$ is chosen from chloride, iodide, methyl sulfate, ethyl sulfate, acetate, and perchlorate.

Among the polychromophoric dyes, non-limiting mention may be made of symmetrical or nonsymmetrical azo and/or azomethine(hydrazone)di- or trichromophoric dyes comprising, on the one hand, at least one optionally fused 5- or 6-membered aromatic heterocycle, comprising at least one quaternized nitrogen atom engaged in said heterocycle and optionally at least one other heteroatom (such as nitrogen, sulfur or oxygen), and, on the other hand, at least one optionally substituted phenyl or naphthyl group, optionally bearing at least one group OR with R being chosen from a hydrogen atom, optionally substituted $C_1$-$C_6$ alkyl radicals, optionally substituted phenyl nucleuses, and $N(R')_2$ with R', which may be identical or different, are chosen from a hydrogen atom, optionally substituted $C_1$-$C_6$ alkyl radicals, and optionally substituted phenyl nucleuses; the radicals R' possibly forming, with the nitrogen atom to which they are attached, a saturated 5- or 6-membered heterocycle, or alternatively one and/or both the radicals R' may each form, with the carbon atom of the aromatic ring located ortho to the nitrogen atom, a saturated 5- or 6-membered heterocycle.

Aromatic cationic heterocycles that may be mentioned include but not limited to, 5- or 6-membered rings comprising 1 to 3 nitrogen atoms and such as comprising 1 or 2 nitrogen atoms, one being quaternized; said heterocycle moreover being optionally fused to a benzene nucleus. It should similarly be noted that the heterocycle may optionally comprise another heteroatom other than nitrogen, for instance sulfur or oxygen.

If the heterocycles or phenyl or naphthyl groups are substituted, they are substituted, for example, with at least one $C_1$-$C_8$ alkyl radical optionally substituted with a hydroxyl, $C_1$-$C_2$ alkoxy, $C_2$-$C_4$ hydroxyalkoxy, acetylamino, or amino group substituted with one or two $C_1$-$C_4$ alkyl radicals optionally bearing at least one hydroxyl group, or the two radicals possibly forming, with the nitrogen atom to which they are attached, a 5- or 6-membered heterocycle, optionally comprising another heteroatom identical to or different than nitrogen; a halogen atom; a hydroxyl group; a $C_1$-$C_2$alkoxy radical; a $C_2$-$C_4$ hydroxyalkoxy radical; an amino radical; an amino radical substituted with one or two identical or different $C_1$-$C_4$ alkyl radicals, optionally bearing at least one hydroxyl group.

These polychromophores are connected together by means of at least one linker optionally comprising at least one quaternized nitrogen atom that may or may not be engaged in a saturated or unsaturated, optionally aromatic heterocycle.

In some embodiments, the at least one linker is a linear, branched or cyclic $C_1$-$C_{20}$ alkyl chain, optionally interrupted with at least one heteroatom (such as nitrogen or oxygen) and/or with at least one group comprising such a heteroatom (CO or $SO_2$), optionally interrupted with at least one heterocycle that may or may not be fused to a phenyl nucleus and comprising at least one quaternized nitrogen atom engaged in said ring and optionally at least one other heteroatom (such as oxygen, nitrogen or sulfur), optionally interrupted with at least one substituted or unsubstituted phenyl or naphthyl group, optionally at least one quaternary ammonium group substituted with two optionally substituted $C_1$-$C_{15}$ alkyl groups; the linker not comprising any nitro, nitroso, or peroxy groups.

The bonding between the linker and each chromophore may take place via a heteroatom substituent on the phenyl or naphthyl nucleus or via the quaternized nitrogen atom of the cationic heterocycle.

The dye may comprise identical or different chromophores.

As examples of such dyes, reference may be made, in a non-limiting manner, to European Patent Application Nos. EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, EP 1 408 919, EP 1 377 264, EP 1 377 262, EP 1 377 261, EP 1 377 263, EP 1 399 425, EP 1 399 117, EP 1 416 909, EP 1 399 116, and EP 1 671 560; International Patent Application Publication Nos. WO 06/063 866, WO 06/063 867, WO 06/063 868, and WO 06/063 869.

It is also possible to use the cationic direct dyes mentioned in European Patent Application No. EP 1 006 153, which describes dyes comprising two chromophores of anthraquinone type connected via a linker of cationic type; European Patent Application Nos. EP 1 433 472, EP 1 433 474, EP 1 433 471 and EP 1 433 473, which describe identical or different dichromophoric dyes, connected via a cationic or noncationic linker, and also European Patent Application No. EP 6 291 333, which describes dyes comprising three chromophores, one of them being an anthraquinone chromophore, to which are attached two chromophores of azo or diazacarbocyanin type or an isomer thereof.

Among the natural direct dyes that may be used according to the present disclosure, non-limiting mention may be made of lawsone, juglone, alizarin, purpurin, carminic acid, kermesic acid, purpurogallin, protocatechaldehyde, indigo, isatin, curcumin, spinulosin, apigenidin, and orceins. It is also possible to use extracts or decoctions containing these natural dyes such as henna-based poultices or extracts.

When they are present, the at least one direct dye may be present in an amount ranging from 0.0001% to 10% by weight, such as from 0.005% to 5% by weight relative to the total weight of the composition.

Cosmetic composition (B) employed in the dyeing process according to the present disclosure may comprise one and/or the other types of dyes. For example, it may optionally result from the mixture of two dye compositions, one comprising the at least one oxidation dye, and the other comprising the at least one direct dye.

Cosmetic composition (B) further comprises at least one ammonium salt.

The ammonium salts that may be used in composition(B) according to the present disclosure include but not limited to ammonium salts ($NH_4^+$).

The ammonium salts that may be used in composition (B) according to the present disclosure may be chosen from the following acid salts: acetate, carbonate, bicarbonate, chloride, citrate, nitrate, nitrite, phosphate, sulfate.

In some embodiments, ammonium carbonate may be used.

In some embodiments, when the process is a lightening process, composition (B) does not comprise any persalts.

When the process is a lightening process, the ammonium salt(s) may be used as a mixture with at least one solid or pasty adjuvant, such as pulverulents. The adjuvants may be chosen from clays, salts other than ammonium salts, anionic, nonionic, cationic or zwitterionic surfactants, natural or synthetic thickeners, optionally modified starch, glass beads, silica, Nylon, alumina, titanium dioxide, zeolites, poly(methyl methacrylate) (PMMA), chitosan, maltodextrin, cyclodextrin, monosaccharides or disaccharides (for instance glucose, sucrose, sorbitol or fructose), zinc oxide, zirconium oxide, silica beads, talc, borosilicates (such as of calcium), polyethylene, polytetrafluoroethylene (PTFE), cellulose and derivatives thereof, superabsorbent compounds, magnesium or calcium carbonates, polyacrylamide, porous hydroxyapatite, sawdust, fucus powder, crosslinked polyvinylpyrrolidone, calcium alginate, active charcoal, poly(vinylidene chloride/acrylonitrile) particles (such as those sold under the general name EXPANCEL® by the company Akzo Nobel under the references EXPANCEL® WE or DE), and mixtures thereof.

In some embodiments, when the process is a lightening process, composition (B) comprises an amount of ammonium salts ranging from 0.1% to 40% by weight, for example, from 0.1% to 20% such as from 0.5% to 20% by weight, relative to the weight of the composition.

In some embodiments, when the process is a dyeing process, then composition (B) comprises an amount of ammonium salts ranging from 0.01% to 30% by weight, for example, ranging from 0.1% to 20% by weight, relative to the weight of the composition.

In some embodiments, composition (B) comprises at least one ammonium salt as a single alkaline agent.

The composition (B) may be an anhydrous or aqueous composition.

The term "aqueous composition" means a composition comprising more than 5% by weight of water, such as more than 10% by weight of water, or further as an example, more than 20% by weight of water.

In some embodiments, the cosmetic composition (B) is an aqueous composition.

In some embodiments, composition (B) contains water. As a non-limiting example, the water concentration may range from 10% to 90% such as from 20% to 80% of the total weight of the composition.

The cosmetic composition (B) may optionally comprise at least one solvent.

Non-limiting examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

The at least one solvent, if it is present, may be present in an amount ranging from 1% to 40% by weight such as ranging from 5% to 30% by weight relative to the weight of the cosmetic composition (B).

In some embodiments, the cosmetic composition (B) may also comprise standard additives such as those that have been listed previously, and reference may be made thereto.

The pH of the cosmetic composition (B), if it is aqueous, ranges from 8 to 11. The pH may be adjusted by using acidifying or basifying agents.

The acidifying agents may be chose from, as non-limiting examples, mineral or organic acids (for instance, hydrochloric acid), orthophosphoric acid, sulfuric acid, carboxylic acids(for instance acetic acid, tartaric acid, citric acid or lactic acid), and sulfonic acids.

The basifying agent, if it is present, may be chosen from the non-salified organic amines and aqueous ammonia. For instance, if the composition contains aqueous ammonia or a salt thereof, then the content of basifying agent(s) is greater than the content of aqueous ammonia (expressed as $NH_3$). If aqueous ammonia is used as basifying agent in composition (B), then the content of aqueous ammonia in the composition (B) will, for example, not exceed 0.03% by weight (expressed as $NH_3$), or as another example, will not exceed 0.01% by weight relative to the weight of the final composition.

In some embodiments, the content of aqueous ammonia in the final composition may not exceed 0.03% by weight (expressed as $NH_3$), such as not exceed 0.01% by weight relative to the weight of the final composition.

It is indicated that the final composition results from the mixing of compositions (A), (B) and (C); this mixture is prepared either before application to the keratin fibers (extemporaneous preparation) or directly on the keratin fibers (successive applications with or without premixing and without intermediate rinsing).

When the process is performed using a premix of compositions (A) and (B) or an extemporaneous preparation obtained by mixing together compositions (A), (B) and (C), then the interval between the mixing and the application to the hair may not exceed 30 minutes, such as 10 minutes or such as 5 minutes.

Finally, the process is performed with a composition (C) comprising at least one oxidizing agent.

In some embodiments, the at least one oxidizing agent is chosen from hydrogen peroxide, urea peroxide, alkali metal bromates, alkali metal ferricyanides, peroxygenated salts (for instance, persulfates, perborates, peracids and precursors thereof), and alkali metal or alkaline-earth metal percarbonates. At least one redox enzyme may also be used as oxidizing agent, and the at least one redox enzyme may be chosen from, for example, laccases, peroxidases, and 2-electron oxidoreductases (such as uricase), optionally in the presence of the respective donor or cofactor thereof.

This oxidizing agent may be formed from hydrogen peroxide, for instance, in aqueous solution (aqueous hydrogen peroxide solution) whose concentration may range, for example, from 0.1% to 50% by weight, such as from 0.5% to 20% by weight, or for instance, from 1% to 15% by weight relative to the oxidizing composition (C).

Depending on the desired degree of lightening, the oxidizing agent may also comprise an oxidizing agent chosen from peroxygenated salts.

The oxidizing composition (C) may or may not be aqueous. The term "aqueous composition" means a composition comprising more than 5% by weight of water, for example, more than 10% by weight of water or more than 20% by weight of water.

In some embodiments, oxidizing composition (C) is an aqueous composition.

It may also comprise at least one organic solvents.

Non-limiting examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

The at least one solvent, if it is present, may be present in an amount ranging from 1% to 40% by weight such as ranging from 5% to 30% by weight relative to the weight of the oxidizing composition (C).

The oxidizing composition (C) may further comprise at least one acidifying agent, such as chosen from those described above.

In some embodiments, the pH of the oxidizing composition (C), when it is aqueous, is less than 7.

The oxidizing composition (C) may further contain other ingredients conventionally used in the field, such as those detailed previously in the context of the anhydrous composition (A) or the composition (B).

Finally, the oxidizing composition (C) is in various forms, for instance, in the form of a solution, an emulsion or a gel.

According to some embodiments of the present disclosure, compositions (A), (B), and (C) are applied to wet or dry keratin fibers, successively and without intermediate rinsing, for example, compositions (A) then (B) and then (C), or (B) then (A) and then (C), are applied.

According to some embodiments of the dyeing method, the composition resulting from the mixing, prior to application, of compositions (A) and (B), and then the oxidizing composition (C), are successively applied and without intermediate rinsing to the keratin fibers.

In accordance with some embodiments of the lightening process, the composition (C) and then the composition resulting from the mixing, prior to application, of compositions (A) and (B), is applied to the keratin fibers, successively and without intermediate rinsing.

In accordance with some embodiments of the process, a composition obtained by extemporaneous mixing, before application, of compositions (A), (B) and (C) is applied to the wet or dry keratin fibers.

In some embodiments, the weight ratios R1 of the amounts of compositions (A)+(B)/(C) and R2 of the amounts of compositions (A)/(B) range from 0.1 to 10 such as from 0.3 to 3.

In some embodiments, the composition obtained after mixing of compositions (A), (B), and (C) is such that, after mixing, the amount of fatty substances is greater than 20% weight, such as greater than 25%, or for example, greater than 30% by weight relative to the total weight of the composition.

In some embodiments, the interval between the mixing and the application to the hair does not exceed 30 minutes, such as 10 minutes or 5 minutes.

In addition, in some embodiments, the mixture present on the fibers (resulting either from the extemporaneous mixing of the compositions, or from the successive application of these compositions) is left in place for a time, from about 1 minute to 1 hour such as from 5 minutes to 30 minutes.

The temperature during the process may range from room temperature (ranging from 15 to 25° C.) to 80° C., for example, from room temperature to 60° C.

After the treatment, the human keratin fibers may be optionally rinsed with water, optionally washed with a shampoo and then rinsed with water, before being dried or left to dry.

Finally, the present disclosure relates to a multi-compartment device comprising a first compartment containing the anhydrous composition (A) comprising at least one fatty substance and at least one above mentioned surfactant, a second compartment comprising a cosmetic composition (B) comprising at least one ammonium salt, and optionally at least one oxidation dye and/or at least one direct dye, and a third compartment comprising a composition (C) comprising at least one oxidizing agent.

The examples that follow serve to illustrate the present disclosure without, however, being limiting in nature.

EXAMPLES

Lightening Process

The following compositions were prepared in which the amounts are expressed in grams.

Anhydrous Composition (A):

| Oxyethylenated (4 EO) sorbitan monolaurate | 21.7 |
|---|---|
| Fumed silica of hydrophobic nature | 11.1 |
| Liquid petroleum jelly | qs 100 |

Cosmetic Composition (B):

| Ammonium carbonate ((NH$_4$)$_2$CO$_3$) | 20 |
|---|---|
| Demineralized water | 80 |

At the time of use, the following were mixed together:
9 parts by weight of anhydrous composition (A)
1 part by weight of composition (B)
10 parts by weight of oxidizing agent Platinium International 20-volumes (6% of hydrogen peroxide) (C)

The resulting mixture had an ammonium carbonate concentration of $1 \times 10^{-2}$ mol % and a pH of 8.7±0.2. This mixture was applied to a natural chestnut-brown lock (tone depth 5) in a mixture/lock bath ratio of 10/1 (g/g).

The leave-on time was 45 minutes at room temperature (about 27° C.).

After this leave-on time, the lock was rinsed, and then washed with ELVIVE multivitamin shampoo.

The implementation of the process according to the present disclosure did not give off any aggressive odor, and led to a good level of lightening.

Dyeing Processes

The following compositions were prepared (amounts expressed in grams):

Anhydrous Composition A:

| Oxyethylenated (4 EO) sorbitan monolaurate | 21.7 |
|---|---|
| Fumed silica of hydrophobic nature | 11.1 |
| Liquid petroleum jelly | qs 100 |

Cosmetic Composition B:

| Ammonium carbonate | 10 |
|---|---|
| para-Phenylenediamine | 1.62 |
| Resorcinol | 1.64 |
| 1-β-Hydroxyethyloxy-2,4-diaminobenzene dihydrochloride | 0.15 |
| Sodium metabisulfite powder | 0.45 |
| Erythorbic acid | 0.31 |
| Ethanol | 8.8 |
| Propylene glycol | 6.2 |
| Hexylene glycol | 3 |
| Dipropylene glycol | 3 |
| Demineralized water | qs 100 |

At the time of use, the following were mixed together:

10 parts by weight of the anhydrous composition (A)

4 parts by weight of composition (B)

15 parts by weight of Platinium International 20-volumes oxidizing agent (6% hydrogen peroxide) (C)

The mixture obtained, the pH of which was about 8, was then applied to a lock of natural hair containing 90% grey hairs (NG) and to a lock of permanent-waved hair containing 90% grey hairs (PWG). The bath ratio "mixture/lock" was, respectively, 10/1 (g/g).

The leave-on time was 30 minutes at 27° C. After this time, the locks were rinsed, and then washed with ELVIVE multivitamin shampoo.

Results

The color of the locks was evaluated in the CIE L*a*b* system using a MINOLTA CM2600D spectrophotometer.

a. Calculation of the Rise or Variation in Colour($\Delta E_{ab}^*$)

The rise in coloration ($\Delta E_{ab}^*$) was evaluated in the CIE L*a*b* system. In this L*a*b* system, L* represents the intensity of the colour, a* represents the green/red colour axis and b* represents the blue/yellow colour axis. The lower the value of L*, the darker or more intense the colour.

In the table below, the value of $\Delta E_{ab}^*$ is calculated from the values of L*a*b according to the following equation (i):

$$\Delta E_{ab}^* = \sqrt{(L^*-L_o^*)^2 + (a^*-a_o^*)^2 + (b^*-b_o^*)^2} \quad \text{(i)}$$

The rise in coloration ($\Delta E_{ab}^*$) was calculated on the locks of natural grey hair (NG) and on the locks of permanent-waved grey hair.

In equation (i), for the locks of natural grey hair (NG), L*, a* and b* represent the values measured on locks of natural grey hair after coloration, and $L_o^*$, $a_o$ and $b_o^*$ represent the values measured on undyed natural grey hair.

In equation (i), for the locks of permanent-waved grey hair (PWG), L*, a* and b* represent the values measured on locks of permanent-waved grey hair after dyeing, and $L_o^*$, $a_o^*$ and $b_o^*$ represent the values measured on locks of undyed permanent-waved grey hair.

The greater the value of $\Delta E_{ab}^*$, the better the rise or variation of the colour.

b. Calculation of the Selectivity

The value of ΔE (selectivity) is calculated from the values of L*, a* and b* measured according to the following equation (ii):

$$\Delta E = \sqrt{(L^*-L_o^*)^2 + (a^*-a_o^*)^2 + (b^*-b_o^*)^2} \quad \text{(ii)}$$

In equation (ii), $L^*$, $a^*$ and $b^*$ represent the values measured on dyed natural grey hair, and $L_0^*$, $a_0^*$ and $b_0^*$ represent the values measured on locks of dyed permanent-waved grey hair.

The coloration selectivity $\Delta E$ corresponds to the variation in color between natural hair, representative of the nature of the hair at the root, and permanent-waved hair, which is representative of the nature of the hair at the end. The lower the value of $\Delta E$, the more uniform the coloration between the end and the root of the hair.

The results are given in the table below.

|  | $L^*$ | $a^*$ | $b^*$ | $\Delta E_{ab}^*$ | $\Delta E$ selectivity |
|---|---|---|---|---|---|
| Lock of untreated natural hair | 60.58 | 0.03 | 12.85 | | |
| Lock of untreated permanent-waved hair | 62.23 | 0.25 | 13.89 | | |
| Lock of natural hair treated with the composition according to the present disclosure | 20.65 | 2.92 | 5.58 | 40.69 | 0.79 |
| Lock of permanent-waved hair treated with the composition according to the present disclosure | 19.94 | 2.75 | 5.28 | 43.26 | |

As seen in the above table, strong and sparingly selective coloration is obtained with the process according to the present disclosure.

Furthermore, no aggressive odor was observed, either during the preparation of the dye mixture, or during the leave-on time on the locks.

What is claimed is:

1. A process for lightening or dyeing keratin fibers comprising applying to the keratin fibers:
   (a) an anhydrous cosmetic composition (A) comprising at least one fatty substance and at least one surfactant,
   (b) a cosmetic composition (B) comprising at least one ammonium salt, and
   (c) a composition (C) comprising at least one oxidizing agent,
      when the process is for dyeing keratin fibers, the cosmetic composition (B) further comprises at least one dye chosen from oxidation dyes and direct dyes.

2. The process according to claim 1, wherein the anhydrous cosmetic composition (A) has a water content of less than 5% by weight relative to the total weight of the anhydrous cosmetic composition (A).

3. The process according to claim 1, wherein the at least one fatty substance is chosen from compounds that are liquid or pasty at room temperature and at atmospheric pressure.

4. The process according to claim 1, wherein the at least one fatty substance is chosen from $C_6$-$C_{16}$ lower alkanes; non-silicone oils of mineral, plant, animal or synthetic origin; fatty alcohols; fatty acids; fatty acid esters; fatty alcohol esters; non-silicone waxes; and silicones.

5. The process according to claim 1, wherein the at least one fatty substance is chosen from liquid petroleum jelly, polydecenes, liquid esters of fatty acids, and liquid esters of fatty alcohols.

6. The process according to claim 1, wherein the at least one fatty substance is present in an amount ranging from 25% to 80% by weight relative to the total weight of the anhydrous cosmetic composition (A).

7. The process according to claim 1, wherein the at least one surfactant is chosen from nonionic surfactants.

8. The process according to claim 7, wherein the nonionic surfactants are chosen from monooxyalkylenated, polyoxyalkylenated, monoglycerolated, and polyglycerolated nonionic surfactants.

9. The process according to claim 1, wherein the at least one ammonium salt is chosen from acetate, carbonate, bicarbonate, chloride, citrate, nitrate, nitrite, phosphate, and sulfate acid salts.

10. The process according to claim 1, wherein the at least one ammonium salt is ammonium carbonate.

11. The process according to claim 1, wherein the at least one ammonium salt is present in an amount ranging from 0.1% to 20% by weight relative to the weight of the cosmetic composition (B).

12. The process according to claim 1, wherein the at least one oxidizing agent is chosen from hydrogen peroxide, urea peroxide, alkali metal bromates, alkali metal ferricyanides, peroxygenated salts, percarbonates of alkali metals, and percarbonates of alkaline-earth metals.

13. The process according to claim 12, wherein the peroxygenated salts are chosen from persulfates, perborates, peracids, and precursors thereof.

14. The process according to claim 1, wherein the compositions (A), (B), and (C) are applied to the keratin fibers successively and without intermediate rinsing.

15. The process according to claim 1, wherein the compositions (A), (B), and (C) are mixed together before applying to the keratin fibers.

16. A multi-compartment device comprising:
   a first compartment comprising the anhydrous cosmetic composition (A) according to claim 1;
   a second compartment comprising a cosmetic composition (B) according to claim 1, and optionally further comprising at least one dye chosen from oxidation dyes and direct dyes;
   a third compartment comprising the cosmetic composition (C) according to claim 1.

* * * * *